(12) United States Patent
Colman et al.

(10) Patent No.: US 6,838,590 B2
(45) Date of Patent: Jan. 4, 2005

(54) PULP FIBER ABSORBENT COMPOSITES FOR PERSONAL CARE PRODUCTS

(75) Inventors: Charles Wilson Colman, Marietta, GA (US); Jaime Braverman, Atlanta, GA (US); Tiffany Marshalle Lee Hunter, Stone Mountain, GA (US); Theresa Michelle McCoy, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 200 days.

(21) Appl. No.: 09/892,408

(22) Filed: Jun. 27, 2001

(65) Prior Publication Data

US 2003/0014026 A1 Jan. 16, 2003

(51) Int. Cl.⁷ .................................................. A61F 13/15
(52) U.S. Cl. ........................................ 604/375; 604/378
(58) Field of Search ................................ 604/365–367, 604/374, 378, 379

(56) References Cited

U.S. PATENT DOCUMENTS

| 3,338,992 A | 8/1967 | Kinney ........................... 264/24 |
| 3,341,394 A | 9/1967 | Kinney ........................... 161/72 |
| 3,502,763 A | 3/1970 | Hartmann ....................... 264/210 |
| 3,542,615 A | 11/1970 | Dobo et al. ..................... 156/181 |
| 3,692,618 A | 9/1972 | Dorschner et al. ............. 161/72 |
| 3,802,817 A | 4/1974 | Matsuki et al. ................. 425/66 |
| 3,849,241 A | 11/1974 | Butin et al. ..................... 161/169 |
| 4,005,957 A | 2/1977 | Savich ............................ 425/80 |

(List continued on next page.)

FOREIGN PATENT DOCUMENTS

| DE | 25 13 251 | 9/1976 | ............. D01F/8/08 |
| DE | 35 08 344 | 9/1986 | ............. A61F/13/00 |
| EP | 0 399 495 | 11/1990 | ............. D04H/1/56 |
| EP | 0 729 735 | 9/1996 | ............. A61F/13/15 |
| EP | 0 640 330 | 5/2000 | ............. A61F/13/46 |
| GB | 2 191 793 | 12/1987 | ............. D01G/23/08 |
| GB | 2 272 859 | 6/1994 | ............. B28B/5/26 |
| GB | 2 294 703 | 5/1996 | ............. A61F/13/15 |
| WO | 93/03699 | 3/1993 | ............. A61F/13/15 |
| WO | 98/24392 | 6/1998 | ............. A61F/13/15 |
| WO | 98/24960 | 6/1998 | ............. D04H/1/54 |
| WO | 98/47456 | 10/1998 | ............. A61F/13/15 |
| WO | 99/63922 | 12/1999 | ............. A61F/13/15 |
| WO | 99/63923 | 12/1999 | ............. A61F/13/15 |
| WO | 99/63925 | 12/1999 | ............. A61F/13/46 |

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

Burgeni and Kapur,–The Textile Research Journal, vol. 37(1967), p. 356.

Chatterjee's Absorbency, Elsevier Science Publishers, B.V. 1985, pp. 36–40..

*Primary Examiner*—John J. Calvert
*Assistant Examiner*—C. Lynne Anderson
(74) *Attorney, Agent, or Firm*—James B. Robinson; Steven D. Flack; Richard M. Shane

(57) ABSTRACT

There is provided a personal care product that has a liquid impermeable backsheet, a liquid permeable topsheet, and an absorbent composite located between the topsheet and backsheet. The absorbent composite has an upper layer made of pulp cellulose fiber in an amount of from 80 to 95 weight percent, at most 20 weight percent binder and has a density between about 0.03 and 0.15 g/cc and a basis weight between about 20 to 75 gsm. The composite has a lower layer having from 80 to 95 weight percent pulp, at most 20 weight percent binder, and has a density greater than the upper layer and between 0.08 and 0.20 g/cc, and a basis weight between 120 and 200 gsm.

15 Claims, 1 Drawing Sheet

U.S. PATENT DOCUMENTS

| | | | |
|---|---|---|---|
| 4,100,324 A | 7/1978 | Anderson et al. | 428/288 |
| 4,223,677 A | 9/1980 | Anderson | 128/287 |
| 4,226,237 A * | 10/1980 | Levesque | 604/374 |
| 4,340,563 A | 7/1982 | Appel et al. | 264/518 |
| 4,375,448 A | 3/1983 | Appel et al. | 264/518 |
| 4,388,056 A | 6/1983 | Lee et al. | 425/83.1 |
| 4,419,403 A | 12/1983 | Varona | 428/288 |
| 4,494,278 A | 1/1985 | Kroyer et al. | 19/304 |
| 4,592,708 A | 6/1986 | Feist et al. | 425/80.1 |
| 4,598,441 A | 7/1986 | Stemmler | 19/145 |
| 4,610,678 A | 9/1986 | Weisman et al. | 604/368 |
| 4,640,810 A | 2/1987 | Laursen et al. | 264/518 |
| 4,673,402 A | 6/1987 | Weisman et al. | 604/368 |
| 4,674,966 A | 6/1987 | Johnson et al. | 425/82.1 |
| 4,738,676 A | 4/1988 | Osborn, III | 604/385 R |
| 4,761,258 A | 8/1988 | Enloe | 264/518 |
| 4,764,325 A | 8/1988 | Angstadt | 264/113 |
| 4,765,780 A | 8/1988 | Angstadt | 406/123 |
| 4,773,903 A | 9/1988 | Weisman et al. | 604/368 |
| 4,781,710 A | 11/1988 | Megison et al. | 604/378 |
| 4,795,668 A | 1/1989 | Krueger et al. | 428/174 |
| 4,818,464 A | 4/1989 | Lau | 264/510 |
| 4,859,388 A | 8/1989 | Peterson et al. | 264/121 |
| 4,865,596 A | 9/1989 | Weisman et al. | 604/368 |
| 4,888,231 A | 12/1989 | Angstadt | 428/213 |
| 4,904,440 A | 2/1990 | Angstadt | 264/517 |
| 4,908,175 A | 3/1990 | Angstadt | 264/113 |
| 4,935,022 A | 6/1990 | Lash et al. | 604/368 |
| 4,950,264 A | 8/1990 | Osborn, III | 604/385.1 |
| 4,988,344 A | 1/1991 | Reising et al. | 604/368 |
| 5,004,579 A | 4/1991 | Wislinski et al. | 264/517 |
| 5,057,368 A | 10/1991 | Largman et al. | 428/397 |
| 5,069,970 A | 12/1991 | Largman et al. | 428/373 |
| 5,108,820 A | 4/1992 | Kaneko et al. | 428/198 |
| 5,108,827 A | 4/1992 | Gessner | 428/219 |
| 5,134,007 A | 7/1992 | Reising et al. | 428/78 |
| 5,200,248 A | 4/1993 | Thompson et al. | 428/131 |
| 5,277,976 A | 1/1994 | Hogle et al. | 428/397 |
| 5,294,478 A | 3/1994 | Wanek et al. | 428/218 |
| 5,294,482 A | 3/1994 | Gessner | 428/287 |
| H1298 H | 4/1994 | Ahr et al. | 428/296 |
| 5,336,552 A | 8/1994 | Strack et al. | 428/224 |
| 5,382,400 A | 1/1995 | Pike et al. | 264/168 |
| 5,383,869 A | 1/1995 | Osborn, III | 604/385.1 |
| 5,387,208 A | 2/1995 | Ashton et al. | 604/378 |
| 5,419,956 A | 5/1995 | Roe | 428/283 |
| 5,422,169 A | 6/1995 | Roe | 428/212 |
| 5,460,622 A * | 10/1995 | Dragoo et al. | 604/378 |
| 5,466,232 A | 11/1995 | Cadieux et al. | 604/378 |
| 5,466,410 A | 11/1995 | Hills | 264/172.11 |
| 5,486,167 A | 1/1996 | Dragoo et al. | 604/384 |
| 5,505,718 A | 4/1996 | Roe et al. | 604/368 |
| 5,509,914 A | 4/1996 | Osborn, III | 604/368 |
| 5,525,407 A * | 6/1996 | Yang | 428/218 |
| 5,527,171 A | 6/1996 | Soerensen | 425/83.1 |
| 5,531,728 A | 7/1996 | Lash | 604/378 |
| 5,540,992 A | 7/1996 | Marcher et al. | 428/373 |
| 5,549,589 A | 8/1996 | Horney et al. | 604/366 |
| 5,562,649 A * | 10/1996 | Chauvette et al. | 604/375 |
| 5,575,786 A | 11/1996 | Osborn, III | 604/387 |
| 5,647,862 A | 7/1997 | Osborn, III et al. | 604/378 |
| 5,649,916 A * | 7/1997 | DiPalma et al. | 604/378 |
| 5,681,300 A | 10/1997 | Ahr et al. | 604/367 |
| 5,752,945 A | 5/1998 | Mosley et al. | 604/370 |
| 5,800,416 A * | 9/1998 | Seger et al. | 604/366 |
| 5,820,973 A | 10/1998 | Dodge, II et al. | 428/212 |
| 5,836,930 A * | 11/1998 | Lantz et al. | 604/378 |
| 5,837,627 A * | 11/1998 | Halabisky et al. | 442/385 |
| 5,866,242 A | 2/1999 | Tan et al. | 428/219 |
| 5,883,231 A | 3/1999 | Achter et al. | 530/362 |
| 5,916,670 A | 6/1999 | Tan et al. | 428/219 |
| 5,922,163 A | 7/1999 | Helynranta et al. | 156/296 |
| 6,407,309 B1 * | 6/2002 | Schilkowski | 604/365 |
| 6,437,214 B1 * | 8/2002 | Everett et al. | 604/378 |
| 6,486,379 B1 * | 11/2002 | Chen et al. | 604/378 |
| 6,562,192 B1 * | 5/2003 | Hamilton et al. | 162/56 |
| 6,737,141 B2 * | 5/2004 | Makolin et al. | 428/57 |

\* cited by examiner

PULP FIBER ABSORBENT COMPOSITES FOR PERSONAL CARE PRODUCTS

BACKGROUND OF THE INVENTION

Personal care products typically are made with a top sheet material (also referred to as a cover sheet or liner) an absorbent core and a liquid impervious back sheet. Some may also have a surge layer or other specialized layers between the top sheet and absorbent core. Absorption of fluid, comfort and avoidance of leakage are the functions desired.

An ideal feminine care product, for example, would have no leakage and deliver comfort and discretion to the user. Current feminine care products may have relatively high leakage and thus offer only modest protection to the consumer. A leak is rather arbitrarily defined in the art, however, as menstrual discharge that stains, contacts or discolors the underwear or body. All leakage is categorized by three key causes: fluid does not absorb into the product, fluid is absorbed into the product but subsequently leaves it, or fluid never contacts the product.

The specific reasons for leakage may be expressed further in terms of definitive mechanisms. A product, for instance, may not have suitable space for absorption due to localized saturation or low contact area. The product may not have a suitable driving force for absorption because the structure does not have the right balance of permeability and capillarity. The interfiber spaces may be partially full of fluid. Fluid may contact the pad and run-off. The fluid may be too viscous or the pores or interfiber spaces are not large enough to allow fluid to pass through to the subjacent layer.

Various attempts have been defined to reduce product leakage. Wings were developed to cover the underwear and thus reduce leakage by reducing the area of the underwear that could be soiled or contacted. Other products have embossing lines or shaping lines which cause the pad to fold in a predefined manner to concentrate fluid loading in a specific area or to increase the contact area of the pad with the body. Still others have attempted to reduce leakage by focusing on side or edge leakage presumably caused by compression of the pad by the legs thereby reducing the contact area of the target zone. These product designs have focused on keeping absorbed fluid away from the edges of the product and directing it toward the center. In many cases this is a function not only of the assembly of materials of different size and shape but also their ability to conform to and contact the body in predefined ways.

In all cases, the material systems and their concentration in a specific product design dramatically impact leakage. In the field of material systems design, leakage is a function of materials shaping and conformability as well as intake, distribution, retention and transfer.

Intake includes the initial absorption of fluid into a dry product as well as the continued uptake of that fluid into the absorbent structure. Development of superior intake systems requires an understanding of environmental conditions including the nature of the fluid and its discharge. Developing functional intake structures requires an understanding of material characteristics and their interaction with the fluid as components and systems of components including interfaces and product design. Product design includes the arrangement and geometric design of material components and their interaction with the body and fluid.

Initial intake of menstrual fluid into an absorbent article is also a function of the characteristics of the liner or topsheet material and the upper absorbent layer.

Intake of menstrual fluid into these materials is a function of the material characteristics including the ratio of void volume to fiber surface area, fiber orientation and fiber surface wettability. These intrinsic material characteristics specifically define the more familiar material properties of permeability, capillarity and fiber wettability which can be calculated and measured by techniques well known in the art. Regardless of the characteristics of the liner, a suitable intermediate layer and absorbent core must be matched to it to permit fluid communication and transfer and thus good fluid intake.

There remains a need for a personal care product that is able to contain the body exudates in such a way as to keep the wearer comfortable and protected from fluid being expressed back onto the wearer or the undergarments.

SUMMARY OF THE INVENTION

In response to the discussed difficulties and problems encountered in the prior art a new absorbent composite has been discovered. Personal care products using this composite are also contemplated to be within the scope of this invention.

One such personal care product has a liquid impermeable backsheet, a liquid permeable topsheet, and an absorbent composite located between the topsheet and backsheet. The absorbent composite has an upper layer made of pulp cellulose fiber in an amount of from 80 to 95 weight percent, at most 20 weight percent binder, and has a density between about 0.03 and 0.15 g/cc and a basis weight between about 20 to 75 gsm. The composite has a lower layer having from 80 to 95 weight percent pulp, at most 20 weight percent binder, and has a density greater than the upper layer and between 0.08 and 0.20 g/cc, and a basis weight between 120 and 200 gsm.

The absorbent composite upper layer may desirably have a density between about 0.04 to 0.10 g/cc and the absorbent composite lower layer may desirably have a density between about 0.10 to 0.15 g/cc.

A more particular embodiment is an absorbent composite having an upper layer made of pulp cellulose fiber in an amount of about 90 weight percent, 10 weight percent binder, and having a density of about 0.04 g/cc and a basis weight of about 50 gsm, and a lower layer having about 90 weight percent pulp, 10 weight percent binder, and having a density of about 0.12 g/cc, and a basis weight of about 150 gsm.

The absorbent composite must have at least two layers and is preferably made according to the airlaying process.

DEFINITIONS

Figure 1:
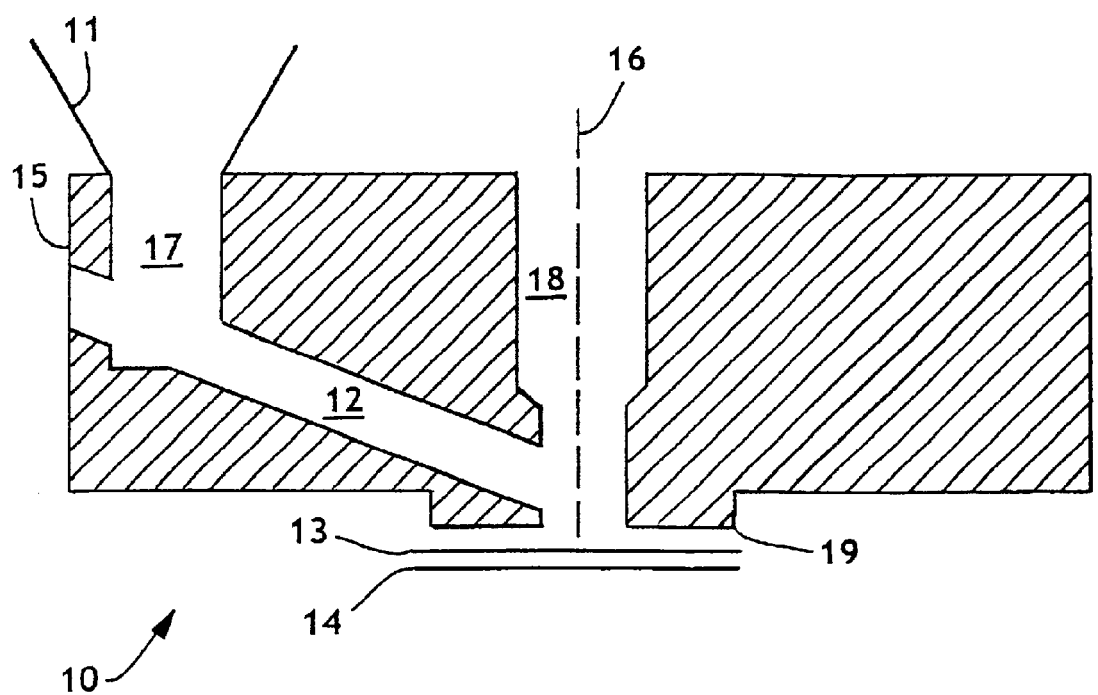
FIG. 1 is a schematic diagram of a rate block apparatus suitable for use in determining fluid intake time of a material or material system.

"Disposable" includes being disposed of after a single use and not intended to be washed and reused.

A "layer" is defined as having a homogeneous composition and density, within typical process variability for nonwoven structures. Alternatively a layer may contain patterns within itself, such as stripes, apertures or waves. "Layer" when used in the singular may have the dual meaning of singular or plural elements.

The "upward" position is closer to the body than "downward" when the article is worn.

"Composite" is defined as having two or more components and may consist of one or more layers. These may be either homogeneous or heterogeneous. It also includes multiple composites that are essentially the same based on structure and surface chemistry.

As used herein and in the claims, the term "comprising" is inclusive or open-ended and does not exclude additional unrecited elements, compositional components, or method steps.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Spunbonded fibers" refers to small diameter fibers that are formed by extruding molten thermoplastic material as filaments from a plurality of fine capillaries of a spinneret. Such a process is disclosed in, for example, U.S. Pat. No. 3,802,817 to Matsuki et al., U.S. Pat. No. 4,340,563 to Appel et al. The fibers may also have shapes such as those described, for example, in U.S. Pat. No. 5,277,976 to Hogle et al. which describes fibers with unconventional shapes.

"Airlaying" is a well-known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive. Airlaying is taught in, for example, U.S. Pat. No. 4,640,810 to Laursen et al.

"Co-aperture" refers to a material that has been apertured, as well as a process of aperturing, wherein two or more materials are apertured together. The apertures extend from top to bottom of the material and are essentially aligned with each other. Co-aperturing can join the materials either temporarily or permanently through entanglement, physical bonding or chemical bonding. Co-aperturing layers may be carried out at ambient or elevated temperatures. Higher temperatures aid the material bonding and create a cleaner pore. One process of co-aperturing is by forcing pins through the various layers by feeding them together through a nip formed by two counter-rotating rollers, one of which has pins to produce the apertures. The apertures may, for example, have a dimension of from 0.5 mm to 5 mm using a pin density of from 1 to 15 apertuers/cm$^2$ and resulting in apertures having an area of less than 19.6 mm$^2$ and an open area ranging from about 2 to about 25 percent. Co-aperturing may be performed as a separate "off-line" operation or as part of a larger converting operation (in-line) depending on process economics and equipment availability.

As used herein, the term "compaction roll" means a set of rollers above and sometimes below the web to compact a just produced web as a way of treating it in order to give it sufficient integrity for further processing. Compactions rolls do not give the relatively strong bonding of secondary bonding processes like through-air bonding, thermal bonding and ultrasonic bonding. Compaction rolls slightly squeeze the web in order to increase its self-adherence and thereby its integrity and density.

"Personal care product" means diapers, wipes, training pants, absorbent underpants, adult incontinence products, feminine hygiene products, wound care items like bandages, and other articles.

"Feminine hygiene products" means sanitary napkins or pads, tampons and panty-liners.

"Target area" refers to the area or position on a personal care product where an insult is normally delivered by a wearer.

Test Methods

Material caliper (thickness): The caliper or thickness of a material, in millimeters, is measured at three different pressures; 0.05, 0.20 and 0.50 Psi, using a Frazier spring model compresometer #326 bulk tester with a 2 inch (50.8 mm) foot (Frazier Precision Instrument Corporation, 925 Sweeney Drive, Hagerstown, Md. 21740). Each type of sample is subjected to five repetitions of testing and the results are averaged to produce a single value.

Density: The density of the materials is calculated by dividing the weight per unit area of a sample in grams per square meter (gsm) by the material caliper in millimeters (mm) at 0.05 psi (3.5 g/cm$^2$) and multiplying the result by 0.001 to convert the value to grams per cubic centimeter (g/cc). A total of three samples would be evaluated and averaged for the density values.

Intake Rewet/Test Procedure (IR): The objective of this test is to determine differences between materials and/or material composites in the rate of intake and the amount of fluid flow back to the surface under pressure when up to three fluid insults are applied, with time allowed for fluid to distribute in the material(s) between insults.

Equipment needed:

2 acrylic rate blocks as shown in FIG. 1. The test apparatus consists of a clear, preferably acrylic, rate block 10 as shown in FIG. 1. The rate block 10 is 3 inches (76.2 mm) wide and 2.87 inches (72.9 mm) deep (into the page) and has an overall height of 1.125 inches (28.6 mm) which includes a center area 19 on the bottom of the rate block 10 that projects farther from the main body of the rate block 10 and has a height of 0.125 inches (3.2 mm) and a width of 0.886 inches (22.5 mm). The rate block 10 has a capillary 12 with an inside diameter of 0.186 inches (4.7 mm) that extends diagonally downward from one side 15 to the center line 16 at an angle of 21.8 degrees from the horizontal. The capillary 12 may be made by drilling the appropriately sized hole from the side 15 of the rate block 10 at the proper angle beginning at a point 0.726 inches (18.4 mm) above the bottom of the rate block 10; provided, however, that the starting point of the drill hole in the side 15 must be subsequently plugged so that test fluid will not escape there. The top hole 17 has a diameter of 0.312 inches (7.9 mm), and a depth of 0.625 inches (15.9 mm) so that it intersects the capillary 12. The top hole 17 is perpendicular to the top of the rate block 10 and is centered 0.28 inches (7.1 mm) from the side 15. The top hole 17 is the aperture into which the funnel 11 is placed. The center hole 18 is for the purpose of viewing the progression of the test fluid and is actually of an oval shape into the plane of FIG. 1. The center hole 18 is centered width-wise on the rate block 10 and has a bottom hole width of 0.315 inches (8 mm) and length of 1.50 inches (38.1 mm) from center to center of 0.315 inch (8 mm) diameter semi-circles making up the ends of the oval. The oval enlarges in size above 0.44 inches (11.2 mm) from the bottom of the rate block 10, for ease of viewing, to a width of 0.395 inches (10 mm) and a length of 1.930 inches (49 mm). The top hole 17 and center hole 18 may also be made by drilling.

P-5000 pipette with RC-5000 tips and foam pipette insert.

Small beaker

Menses simulant (made according to directions below) warmed in bath at 25° C. for 30 minutes or more Small spatula (stirrer)

Bench liner 2 stopwatches 1-2 timers

Gauze squares for cleaning simulant

Procedure: Lay out sample composites according to materials testing plan.

Ply composites are as follows:

Top: Cover—3.5 dpf, 0.6 osy polypropylene spunbond at 0.08 g/cc. Topically treated with 0.3% AHCOVEL® surfactant.

Middle: absorbent composite

Bottom: absorbent core (If a transfer delay layer (TDL) is present it is placed in between the composite and the core), 175 gsm NF401 fluff pulp 1. Weigh each composite dry, record weight. Ply materials back into original configuration.
2. Weigh a dry blotter, record weight and also mark weight on blotter.
3. Place acrylic rate block in middle of sample system.
4. Calibrate pipette:

Weigh a small empty beaker on the balance.

Set pipette to 2 mls.
5. Draw simulant into pipette.

Deliver simulant from pipette into beaker.

If balance indicates 2 grams of simulant was delivered, setting is correct.

If more or less than 2 grams was delivered, decrease or increase the setting and repeat adjusting pipette and weighing the amount of simulant delivered until 2 grams is delivered.

Simulant Handling:

Remove simulant from the refrigerator 30 minutes to 1 hour before using and warm in water bath. Before cutting bag nozzle, massage the bag between hands for a few minutes to mix the simulant, which will have separated in the bag. Cut the bag tubing and pour simulant needed into a small beaker. Stir slowly with a small spatula to mix thoroughly. Return bag to the refrigerator if you do not anticipate using all of it. Return bag to water bath if more will be used during the day.

Test:

Step 1: Center acrylic rate block with funnel on sample. Insult sample system with 2 mls. simulant, using stopwatch to measure the time from the start of the insult until the fluid is absorbed beneath the cover material. Record time. This is the single intake time. Wait 9 minutes from start of insult.

Step 2: For the first sample, repeat Step 1 a second time.

Step 3: For the first sample, repeat Step 1 a third time. This time is referred to as "Triple intake rewet time three" (TIR3) and is reported in seconds Step 4: After the requisite number of insults, weigh each individual material and replace in original system configuration, place sample with a blotter on the rewet stand. Apply 1.0 psi pressure for 3 minutes. Record the weight of the wet blotter. Do not weigh the materials after the rewet portion of the test. The amount of fluid absorbed onto the blotter is termed the rewet value. Low values of rewet are preferred and can be associated with a product or absorbent composite which retains (does not expel) more fluid in its structure under applied loads.

Artificial Menses Preparation: The artificial menses fluid used in the testing was made according to U.S. Pat. No. 5,883,231 from blood and egg white by separating the blood into plasma and red cells and separating the white into thick and thin portions, where "thick" means it has a viscosity after homogenization above about 20 centipoise at 150 $sec^{-1}$, combining the thick egg white with the plasma and thoroughly mixing, and finally adding the red cells and again thoroughly mixing. A more detailed procedure follows:

Blood, in this example defibrinated swine blood, is separated by centrifuging at 3000 rpm for 30 minutes, though other methods or speeds and times may be used if effective. The plasma is separated and stored separately, the buffy coat removed and discarded and the packed red blood cells stored separately as well. It should be noted that the blood must be treated in some manner so that it may be processed without coagulating. Various methods are known to those skilled in the art, such as defibrinating the blood to remove the clotting fibrous materials, the addition or anti-coagulant chemicals and others. The blood must be non-coagulating in order to be useful and any method which accomplishes this without damaging the plasma and red cells is acceptable.

Jumbo chicken eggs are separated, the yolk and chalazae discarded and the egg white retained. The egg white is separated into thick and thin portions by straining the white through a 1000 micron nylon mesh for about 3 minutes, and the thinner portion discarded. The thick portion of egg white, which is retained on the mesh, is collected and drawn into a 60 cc syringe, which is then placed on a programmable syringe pump and homogenized by expelling and refilling the contents five times. The amount of homogenization is controlled by the syringe pump rate of about 100 ml/min, and the tubing inside diameter of about 0.12 inches. After homogenizing the thick egg white has a viscosity of about 20 centipoise at 150 $sec^{-1}$ and is then placed in the centrifuge and spun to remove debris and air bubbles at about 3000 rpm for about 10 minutes After centrifuging, the thick, homogenized egg white, which contains ovamucin, is added to a 300 cc FENWAL® Transfer pack container using a syringe. Then 60 cc of the swine plasma is added to the FENWAL® Transfer pack container. The FENWAL® Transfer pack container is clamped, all air bubbles removed, and placed in a Stomacher lab blender where it is blended at normal (or medium) speed for about 2 minutes. The FENWAL® transfer pack container is then removed from the blender, 60 cc of swine red blood cells are added, and the contents mixed by hand kneading for about 2 minutes or until the contents appeared homogenous. A hematocrit of the final mixture should show a red blood cell content of about 30 weight percent and generally should be at least within a range of 28–32 weight percent for artificial menses made according to this example. The amount of egg white is about 40 weight percent.

The ingredients and equipment used in the preparation of artificial menses are readily available. Below is a listing of sources for the items used, though of course other sources may be used providing they are approximately equivalent.

Blood (swine): Cocalico Biologicals, Inc., 449 Stevens Rd., Reamstown, Pa. 17567, (717) 336–1990.

Fenwal® Transfer pack container, 300 ml, with coupler, code 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-4242.

Hemata Stat-II device to measure hemocrits, serial no. 1194Z03127: Separation Technology, Inc., 1096 Rainer Drive, Altamont Springs, Fla. 32714.

DETAILED DESCRIPTION

The absorbent composites of this invention may be made using the airlaid process. The production of airlaid nonwoven composites is well defined in the literature and documented in the art. Examples include the DanWeb process as described in U.S. Pat. No. 4,640,810 Laursen et al. and assigned to Scan Web of North America Inc, the Kroyer process as described in U.S. Pat. No. 4,494,278 Kroyer et al. and U.S. Pat. No. 5,527,171 Soerensen assigned to Niro Separation a/s, the method of U.S. Pat. No. 4,375,448 Appel et al assigned to Kimberly-Clark Corporation, or other similar methods.

In the practice of this invention an absorbent composite having at least two layers is produced by the airlaid process. The number of layers is set by the equipment constraints as most airlaying equipment currently available has at most four banks of airlaying heads. The composite has an upper layer and a lower layer wherein the upper layer is the layer closer to the body of a wearer while the personal care product is in use. The composite has a gradient of increasing density in the direction away from the wearer when the product is in use.

The upper layer is made of treated or untreated pulp cellulose fiber in an amount of from 80 to 95 weight percent, with at most 20 weight percent binder, has a density between about 0.03 and 0.15 g/cc and a basis weight between about 20 to 75 gsm. Preferably the upper layer has from 85 to 95 weight percent pulp and most preferably about 90 weight percent pulp. Preferably the upper layer has a density of from 0.04 to 0.10 g/cc and most preferably about 0.04 g/cc. Preferably the upper layer has a basis weight from 30 to 60 gsm and most preferably about 50 gsm. The binder is preferably a sheath/core, polyethylene/polyester bicomponent fiber.

The lower layer is made from 80 to 95 weight percent pulp, with at most 20 weight percent binder, has a density greater than the upper layer and between 0.08 and 0.20 g/cc and a basis weight between about 120 to 200 gsm. Preferably the upper layer has from 85 to 95 weight percent pulp and most preferably about 90 weight percent pulp. Preferably the lower layer has a density of from 0.10 to 0.15 g/cc and most preferably about 0.12 g/cc. Preferably the lower layer has a basis weight from 130 to 180 gsm and most preferably about 150 gsm. It is preferable that the lower layer pulp be a sulfite-type pulp though other pulp as shown in the Table may be used.

Binders typically used in these structures help provide mechanical integrity and stabilization. Binders include fiber, liquid or other binder means which may be thermally activated. Preferred fibers for inclusion are those having a relative melting point such as polyolefin fibers. Lower melting point polymers provide the ability to bond the fabric together at fiber cross-over points upon the application of heat. In addition, fibers having a lower melting polymer, like conjugate and biconstituent fibers are suitable for practice of this invention. Fibers having a lower melting polymer are generally referred to as "fusible fibers". By "lower melting polymers" what is meant are those having a glass transition temperature less than about 175 C. It should be noted that the texture of the absorbent web can be modified from soft to stiff through selection of the glass transition temperature of the polymer. Exemplary binder fibers include conjugate fibers of polyolefins, polyamides and polyesters. Some suitable binder fibers are sheath core conjugate fibers available from KoSa Inc. (Charlotte, N.C.) under the designation T-255 and T-256 or Copolyester designation, though many suitable binder fibers are known to those skilled in the art, and are available by many manufacturers such as Chisso and Fibervisions LLC of Wilmington, Del. A particularly suitable co-polyester binder fiber has been developed by KoSa as a sheath core application and is known by designation T-255.

Cellulosic wood pulps include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are fully debonded pulp (NF405) and non-debonded pulp (NB416) and PH Sulfite pulp, also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HPF2 pulp and still another is IP SUPERSOFT® from International Paper Corporation.

One method of making the absorbent composites of this invention is by the airlaying process using water sprays with an overlapping spray pattern to aid in densifying the bottom structure. Vacuum boxes may also be used in conjunction with the water spray to pull the water through the pulp sheet directly under the water spray, and which also aids in a more uniform addition of water to the layer. Compaction rolls, which may be heated, may be used after deposition of each layer to further control the density of the layer and to aid in hydrogen bonding of the layer. The compaction roll temperature is preferably between 180 and 300° F. (82–149° C.) preferably about 200° F. (93° C.). A gap is set between the compaction rolls to achieve the desired density.

The composites of this invention may also be apertured by themselves or co-apertured with a cover. These composites may also be colored to provide a visual cue to the wearer. The color may be desirably added to the polyester fibers.

The composites of this invention were tested according to the intake test and are described in the Table, which also contains the test results. In the Examples in the Table, heated compaction rolls were located in pairs above and below the forming wire after each airlaid head, i.e., after the deposition of each layer, and the composites were made in-line. The rolls were heated to 200° F. and the gap between them adjusted to give the proper web density. Water was also sprayed on the materials to help increase the density and aid in hydrogen bonding. Only a minor amount of water was used; just enough to moisten the web, not to saturate it. Vacuum boxes were located below the forming wire to aid in water deposition.

In the Table, only Examples 4–9 are examples of the invention.

As will be appreciated by those skilled in the art, changes and variations to the invention are considered to be within the ability of those skilled in the art. Such changes and variations are intended by the inventors to be within the scope of the invention.

|  | | Top Layer | | | | | | Bottom Layer | | | | | | Performance | |
|---|---|---|---|---|---|---|---|---|---|---|---|---|---|---|---|
| Example | Basis Wt (gsm) | Density (g/cc) | Total Basis Wt. (gsm) | Density (g/cc) | Bulk (mm) | Pulp Type | Pulp % | Binder % | Total Basis Wt (gsm) | Density (g/cc) | Bulk (mm) | Pulp Type | Pulp % | Binder % | Intake Time Sec. | Rewet weight Grams |
| 1 | 250 | 0.066 | 84 | 0.04 | 2.1 | NF405 | 90 | 10 | 167 | 0.10 | 1.67 | NF401 | 90 | 10 | 34.20 | 0.47 |
| 2 | 250 | 0.072 | 84 | 0.04 | 2.10 | NF405 | 90 | 10 | 167 | 0.12 | 1.39 | NF401 | 90 | 10 | 41.2 | 0.47 |
| 3 | 250 | 0.076 | 84 | 0.04 | 2.10 | NF405 | 90 | 10 | 167 | 0.14 | 1.19 | NF401 | 90 | 10 | 38.2 | 0.5 |
| 4 | 250 | 0.066 | 84 | 0.04 | 2.10 | NF405 | 90 | 10 | 167 | 0.10 | 1.67 | Sulfite | 90 | 10 | 23.4 | 0.2 |
| 5 | 250 | 0.072 | 84 | 0.04 | 2.10 | NF405 | 90 | 10 | 167 | 0.12 | 1.39 | Sulfite | 90 | 10 | 20.2 | 0.23 |
| 6 | 250 | 0.076 | 84 | 0.04 | 2.10 | NF405 | 90 | 10 | 167 | 0.14 | 1.19 | Sulfite | 90 | 10 | 26.8 | 0.22 |
| 7 | 250 | 0.066 | 84 | 0.04 | 2.10 | NF405 | 90 | 10 | 167 | 0.10 | 1.67 | NF416 | 90 | 10 | 29.7 | 0.45 |
| 8 | 250 | 0.072 | 84 | 0.04 | 2.10 | NF405 | 90 | 10 | 167 | 0.12 | 1.39 | NF416 | 90 | 10 | 37.4 | 0.39 |
| 9 | 250 | 0.076 | 84 | 0.04 | 2.10 | NF405 | 90 | 10 | 167 | 0.14 | 1.19 | NF416 | 90 | 10 | 34.6 | 0.41 |
| 10 | 250 | 0.14 | 84 | 0.14 | 0.60 | NF401 | 90 | 10 | 167 | 0.14 | 1.19 | NF401 | 90 | 10 | 30.5 | 0.5 |
| 11 | 250 | 0.072 | 84 | 0.04 | 2.10 | NF401 | 90 | 10 | 167 | 0.10 | 1.67 | NF401 | 90 | 10 | 31 | 0.5 |
| 12 | 250 | 0.072 | 84 | 0.04 | 2.10 | NF401 | 90 | 10 | 167 | 0.12 | 1.39 | NF401 | 90 | 10 | 31.4 | 0.56 |
| 13 | 250 | 0.076 | 84 | 0.04 | 2.10 | NF401 | 90 | 10 | 167 | 0.14 | 1.19 | NF401 | 90 | 10 | 50.6 | 0.51 |

Materials were tested under a 0.6 osy, Ahcovel treated Spunobond top cover and over a 175 gsm homogenous airlaid.
Code 10 is the control

What is claimed is:

1. A personal care product comprising a liquid impermeable backsheet, a liquid permeable topsheet, and an absorbent composite located between said topsheet and said backsheet, said absorbent composite comprising an upper layer made of a debonded pulp in an amount of from 80 to 95 weight percent, at most 20 weight percent binder, and having a density between about 0.03 and 0.15 g/cc and a basis weight between about 20 to 75 gsm, and a lower layer having from 80 to 95 weight percent of a non-debonded or sulfite-type pulp, at most 20 weight percent binder, and having a density greater than said upper layer and between 0.08 and 0.20 g/cc, and a basis weight between 120 and 200 gsm.

2. The personal care product of claim 1 wherein said absorbent composite upper layer has a density between about 0.04 to 0.10 g/cc.

3. The personal care product of claim 2 wherein said absorbent composite lower layer has a density between about 0.10 to 0.15 g/cc.

4. The personal care product of claim 1 wherein said absorbent composite is apertured.

5. The personal care product of claim 1 wherein said absorbent composite is colored via the addition of color to the binder.

6. The personal care product of claim 1 which is a diaper.

7. The personal care product of claim 1 which is a training pant.

8. The personal care product of claim 1 which is an incontinence product.

9. The personal care product of claim 1 which is a bandage.

10. The personal care product of claim 1 which is a feminine hygiene product.

11. An absorbent composite comprising an upper layer made of a debonded pulp in an amount of about 90 weight percent, about 10 weight percent binder, and having a density about 0.04 g/cc and a basis weight of about 50 gsm, and a lower layer having about 90 weight percent of a non-debonded or sulfite-type pulp, about 10 weight percent binder, and having a density of about 0.12 g/cc, and a basis weight of about 150 gsm.

12. A personal care product comprising the absorbent composite of claim 11.

13. The absorbent composite of claim 11 wherein said composite has at least two layers.

14. The absorbent composite of claim 11 wherein said absorbent composite is made according to the airlaying process.

15. A personal care product comprising a liquid impermeable backsheet, a liquid permeable topsheet, and an absorbent composite located between said topsheet and said backsheet, said absorbent composite comprising an upper layer made of fully debonded pulp in an amount of from 80 to 95 weight percent, at most 20 weight percent binder, and having a density between about 0.03 and 0.15 g/cc and a basis weight between about 20 to 75 gsm, and a lower layer having from 80 to 95 weight percent non-debonded pulp, at most 20 weight percent binder, and having a density greater than said upper layer and between 0.08 and 0.20 g/cc, and a basis weight between 120 and 200 gsm.

* * * * *